(12) United States Patent
Merfeld et al.

(10) Patent No.: US 7,789,838 B2
(45) Date of Patent: Sep. 7, 2010

(54) AUDIBLE RANGE OCULOCOMETRY FOR ASSESSMENT OF VESTIBULAR FUNCTION

(75) Inventors: Daniel Michael Merfeld, Lincoln, MA (US); Csilla Haburcakova, Belmont, MA (US); Michael Saginaw, Cambridge, MA (US)

(73) Assignees: Massachusetts Eye & Ear Infirmary, Boston, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 11/756,830

(22) Filed: Jun. 1, 2007

(65) Prior Publication Data

US 2008/0015462 A1    Jan. 17, 2008

Related U.S. Application Data

(60) Provisional application No. 60/803,753, filed on Jun. 2, 2006.

(51) Int. Cl.
*A61B 5/00* (2006.01)
*A61B 5/103* (2006.01)
*A61B 5/117* (2006.01)
*A61B 3/00* (2006.01)
*A61B 3/10* (2006.01)
*A61B 3/14* (2006.01)

(52) U.S. Cl. .............. 600/559; 600/595; 351/200; 351/205; 351/209

(58) Field of Classification Search .............. 600/559, 600/595; 351/200, 205, 209
See application file for complete search history.

(56) References Cited

U.S. PATENT DOCUMENTS

| | | | | |
|---|---|---|---|---|
| 3,864,030 | A * | 2/1975 | Cornsweet | .................. 351/210 |
| 5,218,533 | A | 6/1993 | Schanen | |
| 5,908,393 | A * | 6/1999 | Albrecht et al. | ............. 600/509 |
| 6,547,746 | B1 * | 4/2003 | Marino | ....................... 600/554 |
| 2003/0195588 | A1 | 10/2003 | Fischell et al. | |
| 2004/0097839 | A1 * | 5/2004 | Epley | ......................... 600/595 |
| 2007/0123796 | A1 * | 5/2007 | Lenhardt et al. | ............ 600/561 |

OTHER PUBLICATIONS

Aw, S T. PhD; Todd, M J. MBiomedE; Aw, G E.; Magnussen, J S. Franzcr; Curthoys, I S. PhD; Halmagyi, G M. MD, "Click-evoked vestibulo-ocular reflex: Stimulus-response properties in superior canal dehiscence", Neurology (S.T.A., M.J.T., G.E.A., G.M.H.) and Radiology (J.S.M.), vol. 66(7), Apr. 11, 2006, pp. 1079-1087.*

L.S. Curthoys et al., "Bone conducted vibration selectively activates irregular primary ortholithic vestibular neurons in the guinea pig," *Exp Brain Res* 175:256-267 (2006.

(Continued)

*Primary Examiner*—Max Hindenburg
*Assistant Examiner*—Sean P Dougherty
(74) *Attorney, Agent, or Firm*—Occhiuti Rohlicek & Tsao LLP

(57) ABSTRACT

A method for assessing vestibular system function includes stimulating the inner ear with an audible range signal; collecting data representative of audible range ocular motion; and on the basis of the data, evaluating vestibular system function.

35 Claims, 4 Drawing Sheets

OTHER PUBLICATIONS

M.A. Saginaw, Abstract of poster from NIH Neural Interfaces Workshop (Sep. 7-9, 2005).
M.A. Saginaw, D.M. Merfeld, "Measurable vestibulo-ocular reflexes can be elicited by electrical stimulation at frequencies up to 500 HZ," Program No. 391.20.2005 Abstract Viewer/Itinerary Planner, Washington, DC; Society for Neuroscience, 2005. Online.

E.D. Young et al., "Responses of squirrel monkey vestibular neurons to audio-frequency sound and head vibration," *Acta Otolaryngol* 84:352-360 (1977).

* cited by examiner

SUPRA-THRESHOLD

Freq. (Hz) note data from time of constant stim level, t=8 to t=18 sec

Timeplot Overlay of: Oreo_2006_03_352Hz_95dB.lvb

Time (sec), plotted at the sampling frequency $F_S$ = 12000

Spectra

Freq. (Hz) note data from time of constant stim level, t=14 to t=24 sec

AUDIBLE RANGE OCULOCOMETRY FOR ASSESSMENT OF VESTIBULAR FUNCTION

RELATED APPLICATIONS

Pursuant to 35 USC 119, this application claims the benefit of the priority date of U.S. Patent Application Number 60/803,753, filed Jun. 2, 2006, the contents of which are herein incorporated by reference.

FEDERALLY SPONSORED RESEARCH OR DEVELOPMENT

The U.S. Government may have certain rights in this invention pursuant to Grant No. F31 DC006202 and R01 DC03066 awarded by the National Institute of Health.

FIELD OF INVENTION

This invention relates to medical devices, and in particular, to vestibular diagnostics.

BACKGROUND

The vestibular system is that part of each inner ear that consists of three semicircular canals, which are head rotation sensors, and two otolith organs: the saccule and utricle. The saccule and utricle are sacs lying within the vestibule of the labyrinth. These sacs act as transducers to transform linear acceleration into signals to be communicated to the central nervous system. Because of their complex three-dimensional anatomical structure, the saccule and utricle are sensitive to linear acceleration in all three directions.

When exposed to an acoustic stimulus of sufficient amplitude, the saccule activates the neck muscles. Thus, one can assess saccular function by exposing the patient to an acoustic stimulus, and observing the output of an electromyograph coupled to the neck muscles. This method of testing saccular function is known in the art as the vestibular evoked myogenic potential ("VEMP") test.

A difficulty with the VEMP test is that the measured electromyograph signal is noisy and has large measurement variations. As a result, repeated measurements are often required to obtain an accurate result. This makes the VEMP test time-consuming.

In addition, the amplitude of the acoustic stimulus used in the VEMP test is so high that repeated exposure may damage hearing. Typical thresholds for stimulating a response from the saccule in normal humans are on the order of 90-110 dB SPL. Thresholds for stimulating a response from the utricle and the semicircular canals in patients with certain disorders are even higher. Thus, the repeated exposure to loud acoustic stimuli required to overcome the noisy VEMP measurement can contribute to hearing loss.

The VEMP test also exhibits high variability between patients or between different measurements on the same patient. These variations arise because of differences in neck tension, and electrode placement. In addition, some patients experience nerve and muscle fatigue with repeated stimulation.

SUMMARY

The invention is based on the recognition that high frequency eye-movements provide a window into the functioning of the vestibular system.

In one aspect, the invention includes methods for assessing vestibular system function. Such methods include stimulating the inner ear with an audible range signal; collecting data representative of audible range ocular motion; and on the basis of the data, evaluating vestibular system function.

Practices of the methods include those in which collecting data includes obtaining a video signal representative of ocular motion, those in which collecting data includes obtaining an induction signal representative of ocular motion, and those in which collecting data includes obtaining an electro-oculographic signal representative of ocular motion.

Other practices of the methods also include low-pass filtering the collected data. In some practices, low-pass filtering the collected data includes passing the data through a Bessel filter having cut-off frequencies between 500 and 3000 Hz.

Yet other practices include those in which stimulating the vestibular system includes exposing the vestibular system to an acoustic signal having a fundamental frequency in the audible range, those in which stimulating the vestibular system includes exposing the vestibular system to an electrical signal having a fundamental frequency in the audible range, those in which stimulating the vestibular system includes exposing the vestibular system to bone conduction stimulation having a fundamental frequency in the audible range, those in which stimulating the vestibular system includes exposing the vestibular system to a head vibration having a fundamental frequency in the audible range, and those in which stimulating the vestibular system includes exposing the vestibular system to magnetic stimulation having a fundamental frequency in the audible range.

Additional practices include those in which stimulating the vestibular system includes exposing the vestibular system to a signal having a fundamental frequency between about 250 Hz and 1000 Hz, those in which stimulating the vestibular system includes exposing the vestibular system to a signal having a fundamental frequency above about 50 Hz, and those in which stimulating the vestibular system includes exposing the vestibular system to a signal having a fundamental frequency of about 350 Hz.

Other practices of the method include those in which collecting data includes collecting data indicative of a direction of ocular motion.

Evaluation of vestibular system function can include detecting a variety of conditions, such as disorders of the saccule, the presence of a third window in the inner ear, such as a semicircular canal dehiscence, a fistula, and/or hydrops.

In another aspect, the invention features systems for assessing vestibular function. Such systems include an oculocometer configured to measure audible range eye movements; a vestibular stimulator configured to generate an audible range stimulus; and a data processing system in communication with the oculocometer and the vestibular stimulator, the data processing system being configured to analyze audible range eye movement.

Embodiments of the systems include those in the oculocometer includes a videographic oculocometer, those in which the oculocometer includes an induction oculocometer, and those in which the oculocometer includes an electro-oculograph.

Other embodiments include those in which the vestibular stimulator includes an acoustic signal source, those in which the vestibular stimulator includes an electrical signal source, those in which the vestibular stimulator includes a mechanical stimulator for exposing the vestibular system to bone conduction stimulation, those in which the vestibular stimulator includes a mechanical stimulator for exposing the vestibular system to a head vibration, and those in which the vestibular stimulator includes a magnetic stimulator for exposing the vestibular system to magnetic stimulation.

Yet other embodiments include those in which the vestibular stimulator is configured to generate a stimulus having a fundamental frequency above 50 Hz, those in which the vestibular stimulator is configured to generate a stimulus having a fundamental frequency of about 350 Hz, and those in which the vestibular stimulator is configured to generate a stimulus having a fundamental frequency between 250 Hz and 1000 Hz.

Embodiments of the system include those in which the vestibular stimulator is configured to generate a repetitive stimulus having frequency content in the audible range, and those in which the vestibular stimulator is configured to provide repeated pulsatile stimulation having frequency content in the audible range.

Yet other embodiments also include a filter for filtering data acquired by the oculocometer. One example of a filter is a low-pass filter having a cut-off frequency above 50 Hz. Another example of a filter is a Bessel filter.

These and other features of the invention will be apparent from the following detailed description and the accompanying figures:

DETAILED DESCRIPTION

Figure 1:
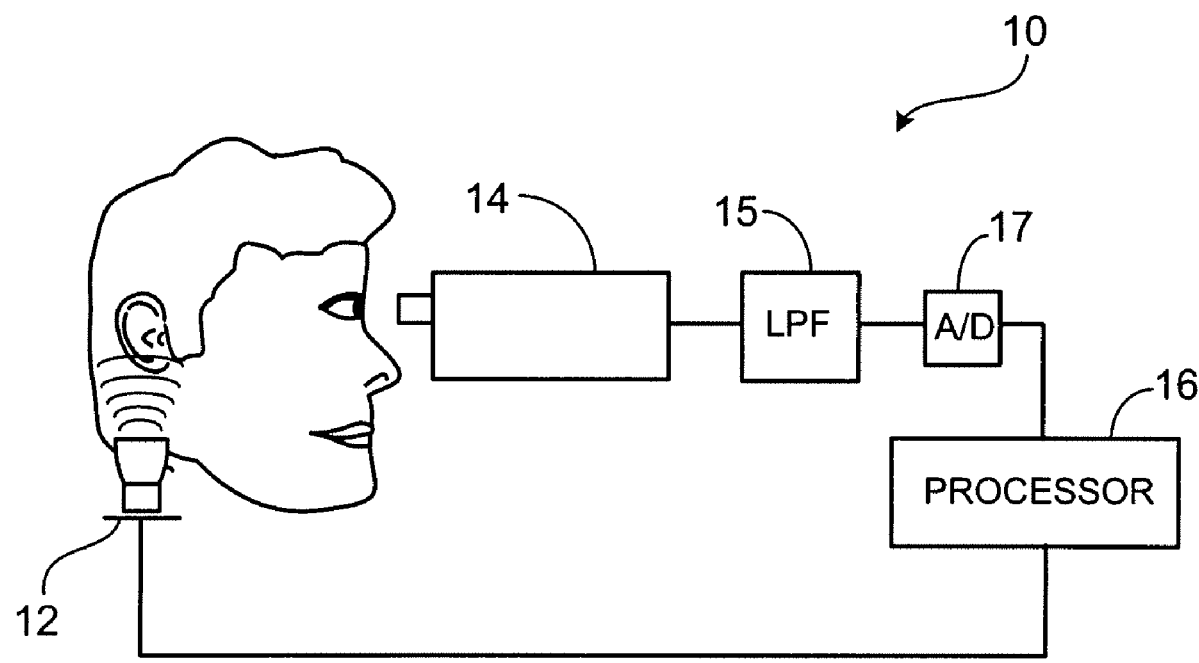
FIGS. 1 and 2 show oculocometric systems.

As shown in FIG. 1, an oculocometric system 10 for assessing saccular function includes a stimulator 12, which evokes eye movement, and an oculocometer 14, which provides data indicative of that eye movement. Both the stimulator 12 and the oculocometer 14 are in communication with a data processing system 16.

In some embodiments, the stimulator 12 is an acoustic stimulator 12 similar to that used in conventional VEMP tests. A typical acoustic stimulator 12 emits an acoustic signal having frequency content in the audible range. A fundamental frequency on the order of 250-1000 Hz is preferred for some applications because the amplitude threshold for stimulating the saccule via acoustic stimulation has been shown to be lower at those frequencies.

In response to an acoustic stimulus, the saccule activates the oculomotor muscles, which move the eye. The frequency of the resultant eye movement is close to the fundamental frequency of the acoustic stimulus. Since the acoustic stimulus is in the audible range, the resulting frequency of ocular motion, or eye movement, is also in the audible range.

The resulting movement of the eye is measured by the oculocometer 14. Since, as noted above, the resulting ocular motion includes response components at audible frequencies, the oculocometer 14 preferably enjoys sufficient temporal resolution to capture movements at audible frequencies.

In addition, the resulting ocular motion is a low amplitude movement. In many cases, the pupil will subtend an angle of no more than two degrees of arc. Thus, the oculocometer 14 preferably enjoys sufficient spatial resolution to capture such low-amplitude movements.

In some embodiments, such as that shown in FIG. 1, the oculocometer 14 is a videographic oculocometer that incorporates a video system in which a video camera is coupled to a machine vision system. Such videographic oculocometers are both non-invasive and offer good spatial resolution. Accordingly, such systems are able to detect small amplitude movements of the eye. However, the temporal resolution of some known video systems is such that some high frequency information may be lost.

In other embodiments, the oculocometer 14 incorporates an electro-oculogram. Such electro-oculographic oculocometers have good temporal resolution. However spatial resolution can in some cases be insufficient to detect low amplitude eye movements.

Another embodiment of the oculocometer 14 is an induction oculocometer that relies on currents induced by movement of a coil that moves with the eye. Induction oculocometric measurements are therefore semi-invasive. However, such measurements combine good temporal and spatial resolution.

In some embodiments, the output of the oculocometer 14 is provided to an anti-alias filter 15, such as a low-pass filter. A suitable low-pass filter is one that minimally distorts its input signal. Examples of such filters include Bessel filters having cut-off frequencies in excess of 50 Hz and Bessel filters with a cut-off frequency of about 3000 Hz. A suitable Bessel filter is a five-pole Bessel filter.

The output of the anti-alias filter 15 is then sampled at an A/D converter 17. The A/D converter 17 samples the filtered signal at a sampling frequency that is at least twice the frequency of the highest frequency component of interest. For example, when the cut-off frequency is 3000 Hz, a suitable sampling frequency is 9000 Hz. The output of the A/D converter 17 is then provided to the data processing system 16.

The data processing system 16 is configured to occasionally transmit an actuation signal to the acoustic stimulator 12 and to receive oculocometric signals from the oculocometer 14. The data processing system 16 then correlates actuation signals with oculocometric signals. Then, the data processing system 16 analyzes the oculometric signal, presents the results to a user on a display and/or stores the data, or parameters representative thereof, in a database. In an exemplary system, data analysis includes Fourier analysis of the oculocometric signal and presentation of the resulting spectral data to a user on a display, as well as the optional storage of spectral response parameters in a database. Alternatively, data analysis includes averaging the eye movements evoked by repetitive stimuli, for example, sinusoids or pulses having high frequency content.

An advantage of the oculocometric system 10 of the type disclosed herein is that the measurement of eye movement generally has lower variability and therefore more repeatability than the measurements available from the VEMP test. As a result, the test period is generally shorter, and the patient need not endure as much exposure to the potentially dangerous acoustic stimulus. In addition, repeatable eye movements are generally easier to measure than myographic potentials, particularly when a videographic oculocometer is used. Furthermore, eye movements occur in different directions. This provides differential diagnostic capabilities, especially for disorders involving the semicircular canals, that are simply not available with neck muscle signals recorded during a VEMP test.

The illustrated system 10 relies on acoustic stimulation to cause high frequency eye movements. However, any other stimulation of the inner ear that causes such audible range eye movements, i.e. eye movements with frequency components in the audible range of 50 Hz-20,000 Hz can be used. Exemplary stimuli include mechanical stimuli, such as head vibrations, bone vibrations, or head taps carried out by, for example, a tendon hammer. Other examples include electric stimulation, and magnetic stimulation.

In addition, although the oculocometric system 10 described herein is used specifically to assess saccular function, there is no restriction on the particular application that the system 10 can be used for. For example, oculocometric systems of the type disclosed and claimed herein can be used to assess the function of the utricle, or other components of the vestibular system.

In one exemplary application, the direction of the high frequency ocular motion provides information indicative of semicircular dehiscence. For example, a vertical movement of the eye during testing with the head held stationary suggests that an attempt is being made to compensate for (non-existent) pitching of the head, whereas a horizontal movement of the eye suggests an attempt to compensate for (non-existent) yaw of the head. The former suggests dehiscence or other malfunction in a semi-circular canal that senses pitch, while the latter suggests dehiscence or other malfunction in the semi-circular canal that senses yaw.

Other exemplary applications include diagnosis of vestibular fistulas, early detection of Meniere's syndrome, as well as diagnosis of other inner ear disorders, for example vestibular hydrops. Another exemplary application is diagnosis of third window disorders, in which a small hole in the bone, sometimes called a third window, leads to abnormal fluid motion in the inner ear, which could be detected by measurement of high frequency eye movements.

EXAMPLE 1

This example discloses measurement of high-frequency eye responses evoked by electrical stimulation.

Stimulation by a prosthetic neural electrical vestibular stimulator may produce undesired side-effects, such as blurred vision. Such blurred vision may arise from eye movements evoked by electrical stimulation. These eye-movements are referred to as "non-compensatory" to distinguish them from compensatory eye movements that provide the brain with a stationary image even as the head moves. One goal of this experiment was to quantify such non-compensatory high-frequency eye movements and to determine whether they diminish with time.

In this experiment, a conductive tip of a Teflon-coated platinum electrode was placed near the ampullary nerve in the lateral semicircular canal of each of four adult male guinea pigs. A head cap for holding the control electronics was also fixed to each guinea pig's head via attachment to a head bolt, which was itself attached to the guinea pig's skull. Finally, a frontal eye coil was placed in one eye of each guinea pig to measure horizontal and vertical eye movements using an induction oculocometer.

In subsequent weeks, the guinea pigs were placed in the dark on a device that held the head cap and head stationary. The vestibular systems of the guinea pigs were stimulated with repeated biphasic charge-balanced current pulses separated from each other by 4 msec. The resulting stimulus, which is an example of a non-acoustic stimulus, therefore had a fundamental frequency of 250 Hz, which is in the audible range. Measurements from the induction oculocometer were low-pass filtered using a 5-pole Bessel filter with a cut-off frequency of 3000 Hz. The resulting signal was then sampled at 9000 Hz.

Spectral analysis of experimental results revealed eye movements having a frequency component at 250 Hz with velocity amplitudes as large as 10 deg/sec. Immobilization of the guinea pig's heads meant that these eye movements could not have been compensatory and were evoked by the high-frequency electrical stimulation.

EXAMPLE 2

This example discloses measurement of high-frequency eye responses evoked by electrical stimulation.

Previous studies have investigated the vestibulo-ocular reflex while physically rotating monkeys and guinea pigs using stimulation frequencies up to approximately 25 Hz. Eye movements were measured at the same frequencies, and the gain has been shown to be approximately constant in a range between 0.1 Hz and 25 Hz.

In an effort to investigate vestibulo-ocular reflex responses at higher frequencies, vestibulo-ocular reflex responses were elicited by stimulating the ampullary nerve innervating a lateral semicircular canal. In one study, electrical stimulation consisted of biphasic current pulses applied at various constant inter-pulse intervals (1.7 to 20 ms), corresponding to pulse rates between 50 and 598 Hz. Such stimuli, if they had been acoustic stimuli, would have been within the audible range. Hence, although the stimuli were electric and not acoustic, they are referred to as audible range stimuli.

In a first study, eye responses were measured at the stimulation frequency for frequencies up to 500 Hz. Measured eye velocity components were in the range from 1 to 10 deg/sec.

In a second study, biphasic current pulses (50 Hz to 598 Hz) were modulated on and off at frequencies between 1 Hz and 149 Hz. Eye movement components were observed at those frequencies in which the input contained spectral line components. Specifically, eye movements were observed at the fundamental modulation frequency and its odd harmonics, and at the biphasic pulse frequency plus and minus odd harmonics of the fundamental frequency.

As in the first study, eye component velocities were in the range from 1 to 10 deg/sec. These responses suggested that even audible range components of the stimulation were transmitted by the nervous system. The vestibulo-ocular reflex sensitivity, which is analogous to the vestibulo-ocular reflex gain measured during rotation, and which is defined as the velocity of the eye movement component divided by the stimulation amplitude at the same frequency, was approximately constant over the entire range of modulation frequencies used.

EXAMPLE 3

The following example discloses measurement of high-frequency eye responses evoked by acoustic stimulation.

Figure 2:
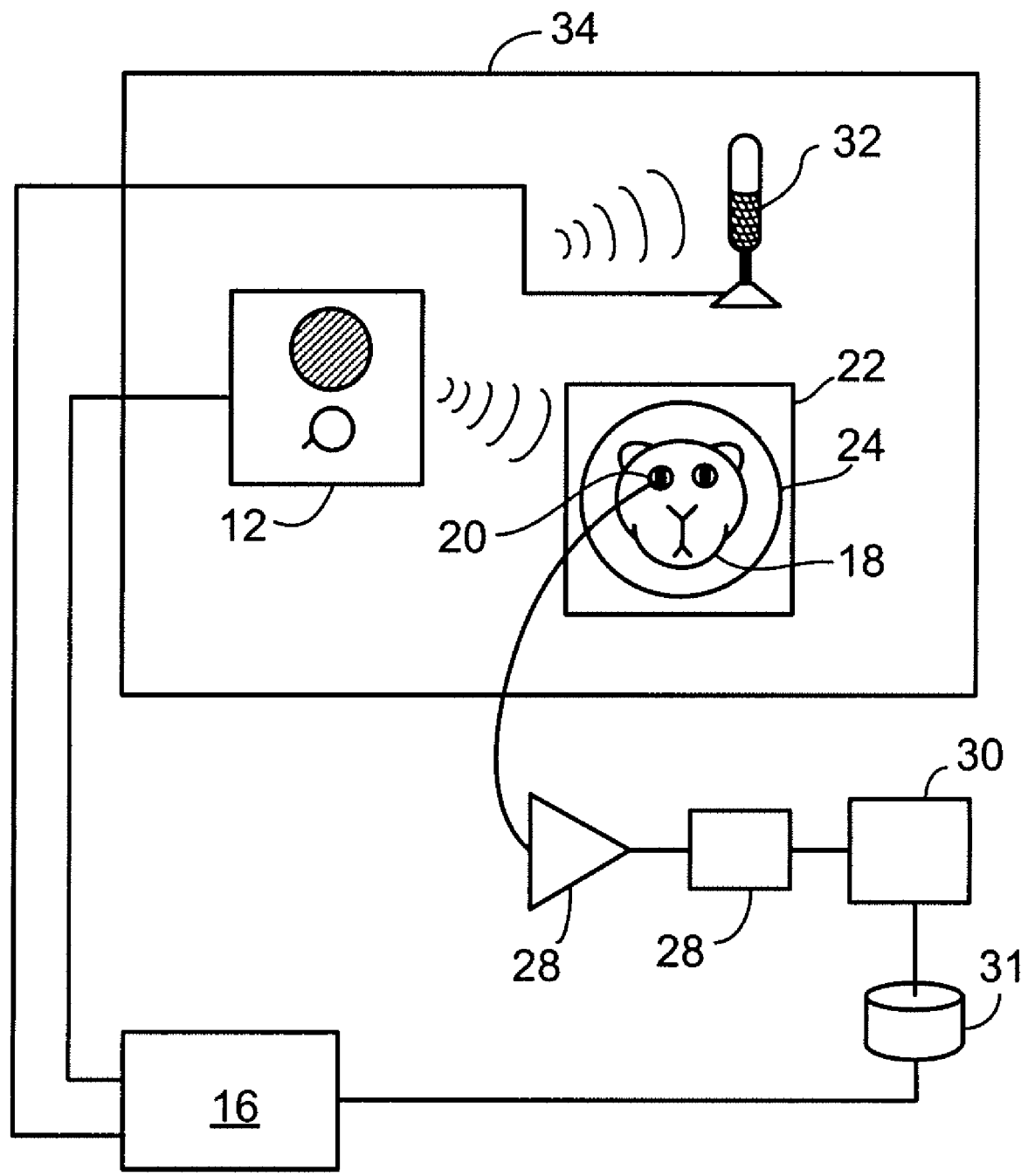
Figure 3A:
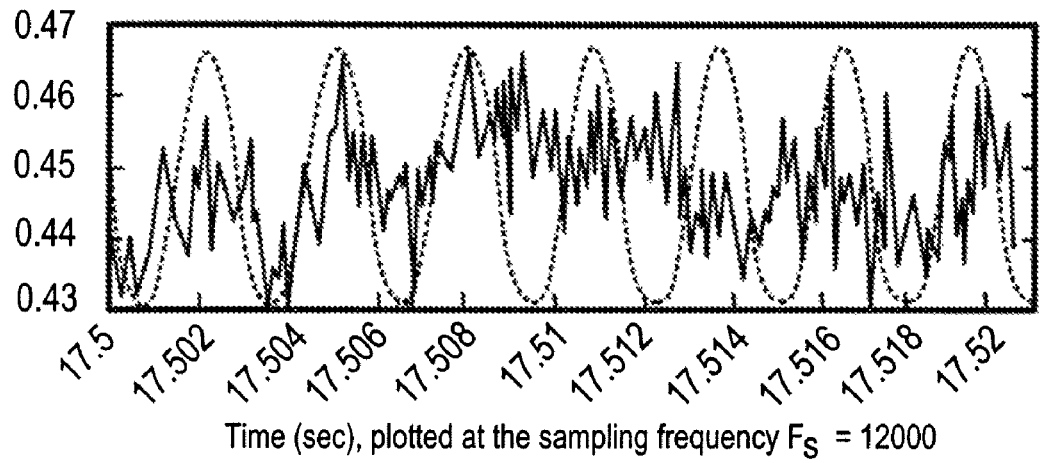
FIG. 3 shows results of an experiment carried out with the oculocometric system of FIG. 2.
Figure 3A:
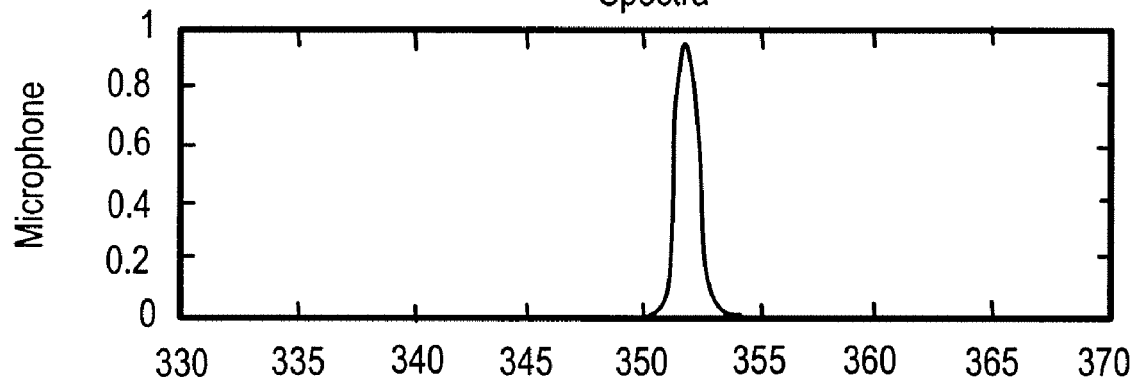
Figure 3A:
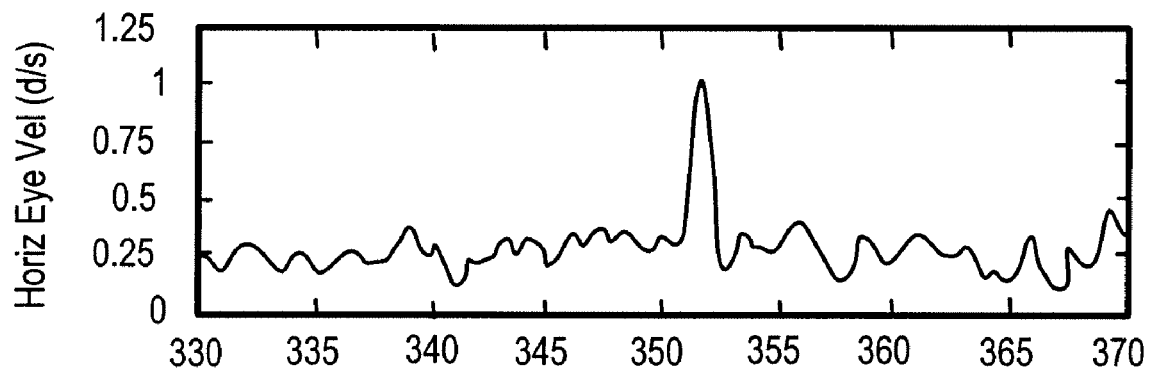
Figure 3B:
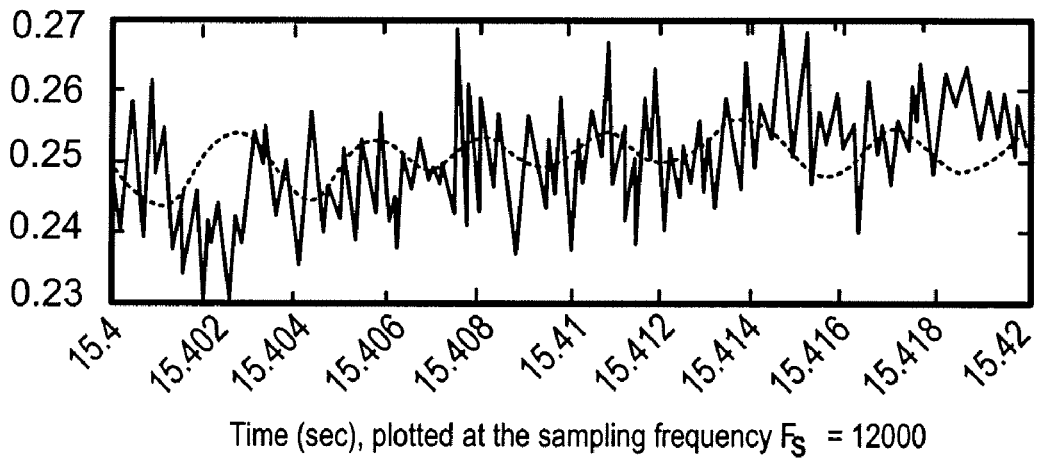
Figure 3B:
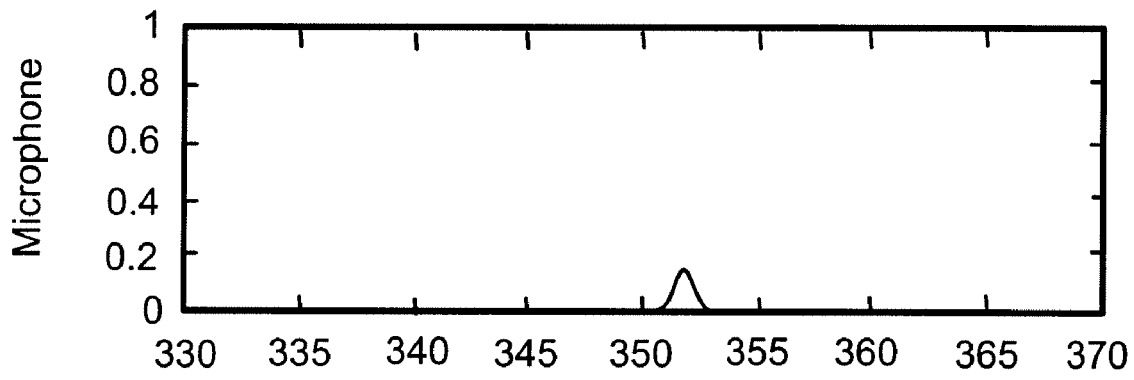
Figure 3B:
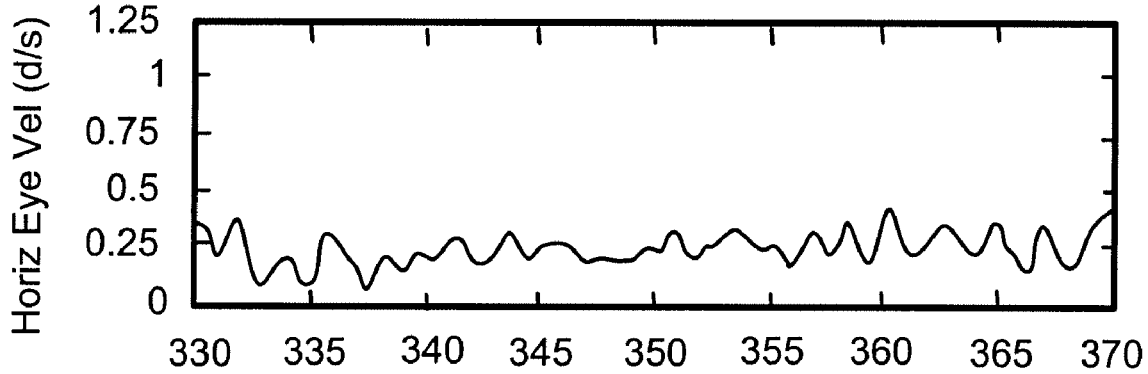

FIG. 2 shows an experimental set-up in which a guinea pig 18, which had an eye on which was implanted a receiving coil 20, was placed in a frame 22 containing a transmitting coil 24. The guinea pig 18 was restrained so that its eyes were centered within the transmitting coil 24.

A time-varying magnetic field generated by the transmitting coil 24 induced a voltage in the receiving coil 20. The magnitude of the induced voltage was proportional to the flux of magnetic field through the receiving coil 20, which in turn depended on the angle of the receiving coil 20 relative to the transmitting coil 24. Thus, the induced voltage provided a measure of the eye movement.

The induced voltage in the receiving coil 20 was amplified by an amplifier 26 and passed through a low pass analog anti-aliasing filter 28, in particular, a 5-pole Bessel filter, having a cut-off frequency at 3 kHz. The output of the filter 28 was then sampled by a sampling circuit 30 at 12 kHz and saved in a data repository 31 for further processing.

An audio speaker 12 provided a sinusoidal acoustic stimulus at a frequency near 350 Hz, the amplitude of which was monitored with a calibrated microphone 32. The frame, speaker 12, microphone 32, and the guinea pig 18 were all isolated in a darkened 60 cm ×90 cm test room 34.

FIG. 3 shows six plots organized into three rows and two columns. The plots in the left-hand column correspond to a sound level of 103 dB, whereas the plots in the right-hand column correspond to sound levels of 95 dB. The first row of plots in FIG. 3 shows the eye position as a function of time, along with a scaled microphone signal. The second row shows the spectrum of the signal received at the microphone. The third row shows spectra corresponding to the time domain eye movement signals in the first row.

It is apparent from inspection of the third row that when the acoustic stimulus is at 103 dB, the oscillation of the eye has a significant component at a frequency close to that of the acoustic stimulus. In contrast, when the acoustic stimulus is only at 95 dB, no such correlation is evident.

The experiment thus suggested that at a threshold between 95 dB and 103 dB, the eye will begin to respond to an acoustic stimulus, and will do so by oscillating at a frequency corresponding to that of the acoustic stimulus.

It is to be understood that while the invention has been described in conjunction with the detailed description thereof, the foregoing description is intended to illustrate and not limit the scope of the invention, which is defined by the scope of the appended claims.

Having described the invention, and a preferred embodiment thereof, what we claim as new, and secured by letters patent is:

Having described the invention, and a preferred embodiment thereof, what we claim as new, and secured by letters patent is:

1. A method for assessing vestibular system function, the method comprising:
    stimulating at least one of the saccule and utricle with an audible range signal thereby causing activation of ocular muscles to cause ocular motion,
    collecting data representative of the ocular motion, said collected data including data that represents frequency components of the ocular motion that are between 50 Hz to 20,000 Hz; and
    based on the data representative of the ocular motion, evaluating vestibular system function.

2. The method of claim 1, wherein collecting data comprises obtaining a video signal representative of the ocular motion.

3. The method of claim 1, wherein collecting data comprises obtaining an induction signal representative of the ocular motion, the induction signal being provided by an induction oculometer that relies on currents induced by movement of a coil that moves with the eye.

4. The method of claim 1, wherein collecting data comprises obtaining an electro-oculographic signal representative of the ocular motion.

5. The method of claim 1, further comprising low-pass filtering the collected data.

6. The method of claim 5, wherein low-pass filtering the collected data comprises passing the data representative of ocular motion through a Bessel filter having a cut-off frequency between 500 and 3000 Hz.

7. The method of claim 1, wherein stimulating the vestibular system comprises exposing the vestibular system to an acoustic signal having a fundamental frequency in an audible range.

8. The method of claim 1, wherein stimulating the vestibular system comprises exposing the vestibular system to an electrical signal having a fundamental frequency in an audible range.

9. The method of claim 1, wherein stimulating the vestibular system comprises exposing the vestibular system to bone conduction stimulation having a fundamental frequency in an audible range.

10. The method of claim 1, wherein stimulating the vestibular system comprises exposing the vestibular system to a head vibration having a fundamental frequency in an audible range.

11. The method of claim 1, wherein stimulating the vestibular system comprises exposing the vestibular system to magnetic stimulation having a fundamental frequency in an audible range.

12. The method of claim 1, wherein stimulating the vestibular system comprises exposing the vestibular system to a signal having a fundamental frequency between about 250 Hz and 1000 Hz.

13. The method of claim 1, wherein stimulating the vestibular system comprises exposing the vestibular system to a signal having a fundamental frequency above about 50 Hz.

14. The method of claim 1, wherein stimulating the vestibular system comprises exposing the vestibular system to a signal having a fundamental frequency of about 350 Hz.

15. The method of claim 1, wherein collecting data comprises collecting data indicative of a direction of ocular motion.

16. A system for assessing vestibular function, the system comprising:
    an oculocometer configured to measure frequency components of eye movements, said frequency components being between 50 Hz and 20,000 Hz;
    a vestibular stimulator configured to generate an audible range stimulus for stimulating at least one of the utricle and saccule thereby causing activation of oculomotor muscles, said oculomotor muscles causing ocular motion having frequency components between 50 Hz and 20,000 Hz; and
    a data processing system in communication with the oculocometer and the vestibular stimulator, the data processing system being configured to receive, from said oculocometer, data representing ocular motion caused by said audible range stimulus generated by said vestibular stimulator and to analyze the frequency components of eye movements caused by said audible range stimulus generated by said vestibular stimulator, said frequency components being between 50 Hz and 20,000 Hz.

17. The system of claim 16, wherein the oculocometer comprises a videographic oculocometer.

18. The system of claim 16, wherein the oculocometer comprises au induction oculocometer.

19. The system of claim 16, wherein the vestibular stimulator comprises an acoustic signal source.

20. The system of claim 16, wherein the vestibular stimulator comprises an electrical signal source.

21. The system of claim 16, wherein the vestibular stimulator comprises a mechanical stimulator for exposing the vestibular system to bone conduction stimulation.

22. The system claim 16, wherein the vestibular stimulator comprises a mechanical stimulator for exposing the vestibular system to a head vibration.

23. The system of claim 16, wherein the vestibular stimulator comprises a magnetic stimulator for exposing the vestibular system to magnetic stimulation.

24. The system of claim 16, wherein the vestibular stimulator is configured to generate a stimulus having a fundamental frequency above 50 Hz.

25. The system of claim 16, wherein the vestibular stimulator is configured to generate a stimulus having a fundamental frequency of about 350 Hz.

26. The system of claim 16, wherein the vestibular stimulator is configured to generate a stimulus having a fundamental frequency between 250 Hz and 1000 Hz.

27. The system of claim 16, wherein the vestibular stimulator is configured to generate a repetitive stimulus having frequency content in an audible range.

28. The system of claim 16, wherein the vestibular stimulator is configured to provide repeated pulsatile stimulation having frequency content in an audible range.

29. The system of claim 16, further comprising a filter for filtering data acquired by the oculocometer.

30. The system of claim 29, wherein the filter comprises a low-pass filter having a cut-off frequency above 50 Hz.

31. The system of claim 30, wherein the low-pass filter comprises a Bessel filter.

32. A system for assessing vestibular function, the system comprising:
    means for measuring frequency components of eye movements, said frequency components being between 50 hz, and 20,000 Hz;
    means for stimulating at least one of the utricle and saccule with an audio range stimulus, thereby causing activation of oculomotor muscles, said oculomotor muscles causing movements having frequency components between 50 Hz and 20,000 Hz; and
    a data processing system in communication with the measuring means and the stimulating means, the data processing system being configured to receive, from the measurement means, data representing ocular motion caused by said audible range stimulus generated by said stimulating means and to analyze the frequency components of eye movements caused by said audio range stimulus provided by said stimulating means, said frequency components being between 50 Hz and 20,000 Hz.

33. The method of claim 1, further comprising performing a Fourier analysis of the data representative of ocular motion, and displaying resulting spectral data.

34. The method of claim 1, wherein collecting data representative of ocular motion comprises collecting data representative of pupil motion that subtends an angle of no more than two degrees of arc.

35. The method of claim 1, wherein stimulating the vestibular system comprises applying a plurality of repetitive stimuli, and wherein collecting data representative of ocular motion comprises averaging eye movements evoked by the repetitive stimuli.

* * * * *